(12) United States Patent
Gogolak et al.

(10) Patent No.: US 7,539,684 B2
(45) Date of Patent: May 26, 2009

(54) PROCESSING DRUG DATA

(75) Inventors: Victor V. Gogolak, McLean, VA (US); Lara Gogolak, McLean, VA (US)

(73) Assignee: QED Solutions, Inc., McLean, VA (US)

( * ) Notice: Subject to any disclaimer, the term of this patent is extended or adjusted under 35 U.S.C. 154(b) by 850 days.

(21) Appl. No.: 09/683,828

(22) Filed: Feb. 20, 2002

(65) Prior Publication Data
US 2002/0188465 A1  Dec. 12, 2002

Related U.S. Application Data

(63) Continuation-in-part of application No. 09/681,587, filed on May 2, 2001, now Pat. No. 6,778,994.

(51) Int. Cl.
*G06F 17/30* (2006.01)

(52) U.S. Cl. .......................... 707/100; 704/9

(58) Field of Classification Search ............... 707/1–3, 707/10, 100, 102, 104.1, 101; 706/15; 717/143; 704/9
See application file for complete search history.

(56) References Cited

U.S. PATENT DOCUMENTS

| | | | |
|---|---|---|---|
| 4,384,329 A | 5/1983 | Rosenbaum et al. |
| 5,299,121 A | 3/1994 | Brill et al. |
| 5,337,919 A | 8/1994 | Spaulding et al. |
| 5,371,807 A | 12/1994 | Register et al. |
| 5,495,604 A | 2/1996 | Harding et al. |
| 5,502,576 A | 3/1996 | Ramsay et al. |
| 5,583,758 A | 12/1996 | McIlroy et al. |
| 5,592,668 A | 1/1997 | Harding et al. |
| 5,594,637 A | 1/1997 | Eisenberg et al. |
| 5,634,053 A | 5/1997 | Noble et al. |
| 5,642,731 A | 7/1997 | Kehr |
| 5,659,731 A | 8/1997 | Gustafson |
| 5,664,109 A | 9/1997 | Johnson et al. |
| 5,692,171 A | 11/1997 | Andres |
| 5,737,539 A | 4/1998 | Edelson et al. |

(Continued)

FOREIGN PATENT DOCUMENTS

| | | |
|---|---|---|
| JP | 10-225500 | 8/1998 |
| JP | 11-282934 | 10/1999 |

OTHER PUBLICATIONS

LipShutz, Seymour, Ph.D. (1968). "Theory and Problems of Linear Algebra," Schaum's Outline Series, McGraw-Hill Book Company, 5 pp.

(Continued)

*Primary Examiner*—Cheryl Lewis
(74) *Attorney, Agent, or Firm*—Morrison & Foerster LLP

(57) ABSTRACT

Computer-assisted methods and systems of processing a drug information source. Characterizing the drug by the set comprising: syntax-parsed drug rule elements, adverse event data, mapped terms, and metadata. A method includes: creating a drug rule syntax; extracting metadata from the drug information source; extracting verbatim adverse event data from the drug information source; identifying drug rule content from the drug information source; mapping terms from verbatim data to a reference source; and parsing drug rule elements from at least one identified instance of drug rule content into the drug rule syntax, retaining associations between those drug rule elements that form a drug rule.

16 Claims, 12 Drawing Sheets

U.S. PATENT DOCUMENTS

| | | | |
|---|---|---|---|
| 5,758,095 | A | 5/1998 | Albaum et al. |
| 5,804,803 | A | 9/1998 | Cragum et al. |
| 5,833,599 | A | 11/1998 | Schrier et al. |
| 5,845,255 | A * | 12/1998 | Mayaud .................. 705/3 |
| 5,860,917 | A | 1/1999 | Comanor et al. |
| 5,864,789 | A | 1/1999 | Lieberman et al. |
| 5,911,132 | A | 6/1999 | Sloane |
| 5,924,074 | A | 7/1999 | Evans |
| 6,000,828 | A | 12/1999 | Leet |
| 6,014,631 | A | 1/2000 | Teagarden et al. |
| 6,067,524 | A | 5/2000 | Byerly et al. |
| 6,076,083 | A | 6/2000 | Baker |
| 6,076,088 | A | 6/2000 | Paik et al. |
| 6,082,776 | A | 7/2000 | Feinberg |
| 6,108,635 | A | 8/2000 | Herren et al. |
| 6,112,182 | A | 8/2000 | Akers et al. |
| 6,120,443 | A | 9/2000 | Cohen-Laroque |
| 6,137,911 | A | 10/2000 | Zhilyaev |
| 6,151,581 | A | 11/2000 | Kraftson et al. |
| 6,188,988 | B1 * | 2/2001 | Barry et al. ............ 705/3 |
| 6,219,674 | B1 | 4/2001 | Classen |
| 6,226,564 | B1 | 5/2001 | Stuart |
| 6,263,329 | B1 | 7/2001 | Evans |
| 6,317,719 | B1 | 11/2001 | Schrier et al. |
| 6,446,081 | B1 | 9/2002 | Preston |
| 6,507,829 | B1 * | 1/2003 | Richards et al. .......... 706/45 |
| 6,658,396 | B1 * | 12/2003 | Tang et al. ............ 706/17 |
| 6,684,221 | B1 | 1/2004 | Rejndrup |
| 6,697,783 | B1 | 2/2004 | Brinkman et al. |
| 2001/0049673 | A1 * | 12/2001 | Dulong et al. ............ 707/1 |
| 2002/0010595 | A1 * | 1/2002 | Kapp .................... 705/2 |
| 2002/0040282 | A1 | 4/2002 | Bailey et al. |
| 2002/0120350 | A1 | 8/2002 | Klass et al. |
| 2002/0129031 | A1 | 9/2002 | Lau et al. |
| 2002/0169771 | A1 * | 11/2002 | Melmon et al. ............ 707/5 |
| 2003/0040662 | A1 | 2/2003 | Keys |

OTHER PUBLICATIONS

Anderson, T.W. (1972). "A Bibliography of Multivariate Statistical Analysis," Oliver & Boyd, Edinburgh, 3 pp.

Darlington, Richard B. (1990). "Regression and Linear Models," McGraw-Hill Publishing Company, 15 pp.

Press, James S. and Wilson, Sandra. (1978). "Choosing Between Logistic Regression and Discriminant Analysis," Journal of the American Statistical Association, vol. 73, pp. 699-705.

Kosko, Bart. (1992). "Neural Networks and Fuzzy Systems—A Dynamical Systems Approach to Machine Intelligence," Prentice Hall, Englewood Cliffs, NJ, 11 pp.

(Apr. 10, 1997). Multum Releases Web-Based MediSource Lexicon; Downloadable Drug Product and Disease Listings Database,: PR Newswire, 2 pp.

(Nov. 1998). "Post-Marketing Surveillance for Adverse Events After Vaccination: The National Vaccine Adverse Event Reporting System (VAERS)," Medwatch, 12 pp.

(Apr. 12, 1999). "The Totally Unauthorized, Completely Repudiated, Bootlegged, Unsupported, Undocumented, Insider's Post-Pre-Alpha Guide to Multum's Lexicon," Multum Information Services, Inc., Copyright 1997-1999 (Rev. 3.d), pp. 1-49.

DuMouchel, William. (1999) "Bayesian Data Mining in Large Frequency Tables, with an Application to FDA Spontaneous Reporting System," The American Statistician, vol. 53 (No. 3): 31 pp.

Szarfman, Ana, M.D., Ph.D. (1999). "New Methods for Signal Detection," Proceedings of the 15th International Conference on Pharmacoepidemiology, 56 pp.

Mootrey, Gina et al.(1999) "Chapter 18: Surveillance for Adverse Events Following Vaccination," VPD Surveillance Manual, 20 pp.

Andrews, Michelle, "Prescription for Disaster", SmartMoney, pp. 124-129, May 2001.

"Vaccine Adverse Event Reporting System (VAERS)" [online], U.S. Department of Health and Human Services, Jul. 2001, located at http://www.vaers.org/search/README retrieved [Jul. 2001]. (12 pp.).

Szarfman, Ana, M.D., Ph.D., "Application of screening Algorithms and Computer Systems to Efficiently Signal Combinations of Drugs and Events in FDA's Spontaneous Reports" [online], http://apha.confex.com/apha/129.am/techprogram/paper_32272 retrieved [Oct. 22, 2001]. (2 pp.).

"VAERS Data: Guide to Interpreting Case Report Information Obtained From Vaccine Adverse Event Reporting System (VAERS)" [online], http://www.vaers.org/info retrieved [Jun. 11, 2002]. (2 pp.).

PDR.net [online], Copyright 2002, http://www.pdr.net/HomePage_template.jsp retrieved [Aug. 22, 2002]. (1 p.).

Epocrates [online], Copyright 2002, http://www.multum.com retrieved on [Aug. 22, 2002]. (1 p.).

Multum Trusted Health Information [online] http://www.multum.com retrieved on [Aug. 22, 2002]. (1 p.).

International Search Report for Application No. PCT/US02/13666, dated Jul. 16, 2002 (mailing date).

International Search Report for Application No. PCT/US02/13662, dated Jul. 15, 2002 (mailing date).

* cited by examiner

| Category | Lexical Element | Lexical Element | Lexical Element |
|---|---|---|---|
| Risk factor (RF) patient history | | | |
| Risk due to past history | | | |
| RF patient ADR history | Sepsis | Hypersensitivity | Hypersensitivity |
| RF patient family history | | | |
| RF patient concurrent condition | | | |
| Risk due to current disease | | | |
| RF past drug | | Enbrel | <Enbrel component> |
| RF past drug class | | | |
| RF concomitant drug | | | |
| RF concomitant drug class | | | |
| RF drug-in-question (DIQ) class | DMARD | DMARD | DMARD |
| RF DIQ | Enbrel (etanercept) | Enbrel (etanercept) | Enbrel (etanercept) |
| RF difference of gender | | | |
| RF age | | | |
| Outcome | Sepsis | Hypersensitivity | Hypersensitivity |
| Outcome origin | | | |
| Notes on outcome and resolution | | | |
| Prescribing action for DIQ | Contraindication | Contraindication | Contraindication |
| Follow-up actions | | | |
| Follow-up actions cont'd | | | |
| Conditional follow-up actions | | | |
| FUA condition | | | |
| FUA conditional action | | | |
| Instructions to patient | | | |
| Conditional instructions to patient | | | |
| ITP condition | | | |
| ITP conditional action | | | |
| What to remain alert for | | | |
| Not to be used as alternate therapy for | | | |
| Parameters to monitor | | | |
| What to test or check | | | |
| When to test or check | | | |
| Why/what to consider | | | |
| Prescribing notes to Physician | | | |

FIGURE 3

| Category | Lexical Element | Lexical Element |
|---|---|---|
| Risk factor (RF) patient history | | |
| Risk due to past history | | |
| RF patient ADR history | | |
| RF patient family history | | |
| RF patient concurrent condition | | |
| Risk due to current disease | | |
| RF past drug | | |
| RF past drug class | | |
| RF concomitant drug | | |
| RF concomitant drug class | | |
| RF drug-in-question (DIQ) class | DMARD | DMARD |
| RF DIQ | Enbrel | Enbrel |
| RF difference of gender | | |
| RF age | | |
| Outcome | New infection | sepsis |
| Outcome origin | | |
| Notes on outcome and resolution | | |
| Prescribing action for DIQ | Continue | Discontinue |
| Follow-up actions | Monitor closely | |
| Follow-up actions cont'd | | |
| Conditional follow-up actions | Discontinue if new infection becomes serious | |
| FUA condition | | |
| FUA conditional action | | |
| Instructions to patient | | |
| Conditional instructions to patient | | |
| ITP condition | | |
| ITP conditional action | | |
| What to remain alert for | | |
| Not to be used as alternate therapy for | | |
| Parameters to monitor | | |
| What to test or check | | |
| When to test or check | | |
| Why/what to consider | | |
| Prescribing notes to Physician | | |

FIGURE 4

Figure 5: Sample of mapping a conditional text statement to a rule structure, using dictionary terms Label Text: Celebrex should not be given to patients who have demonstrated allergic-type reactions to sulfonomides.

| Field | Value |
|---|---|
| Risk Category | |
| Risk Factor Patient past history | |
| Risk Factor Patient ADR history | Allergic-type reactions |
| Risk factor Patient family history | |
| Risk Factor Patient concurrent condition | |
| Risk factor Past drug | |
| Risk factor Past Drug Class | Sulfonomides |
| Risk Factor Concomitant Drug | |
| Risk Factor Concomitant drug class | |
| Risk Factor Drug-in-Question Class | |
| Risk factor Drug-in-Question | Celebrex |
| Outcome | |
| Outcome Origin | |
| Additional Notes on Outcome and Resolution | |
| Prescribing Action for Drug-in-Question | Contraindicated |
| Follow-up Actions | |
| Follow-up Actions cont'd | |
| Conditional Follow-up Actions | |
| FUA Condition | |
| FUA Conditional action | |
| Instructions to Patient | |
| Conditional Instructions to Patient | |
| ITP Condition | |
| ITP Conditional action | |
| What to Remain Alert For | |
| Not to be used as Alternate Therapy For | |
| Parameters to Monitor | |
| What to Test/Check | |
| When to Test/Check | |
| Why/What to Consider | |
| Additional Prescribing Note to Physician | |
| Note General | |

Figure 6: Sample of mapping a complex conditional text statement to a rule structure, using dictionary terms
Label Text:
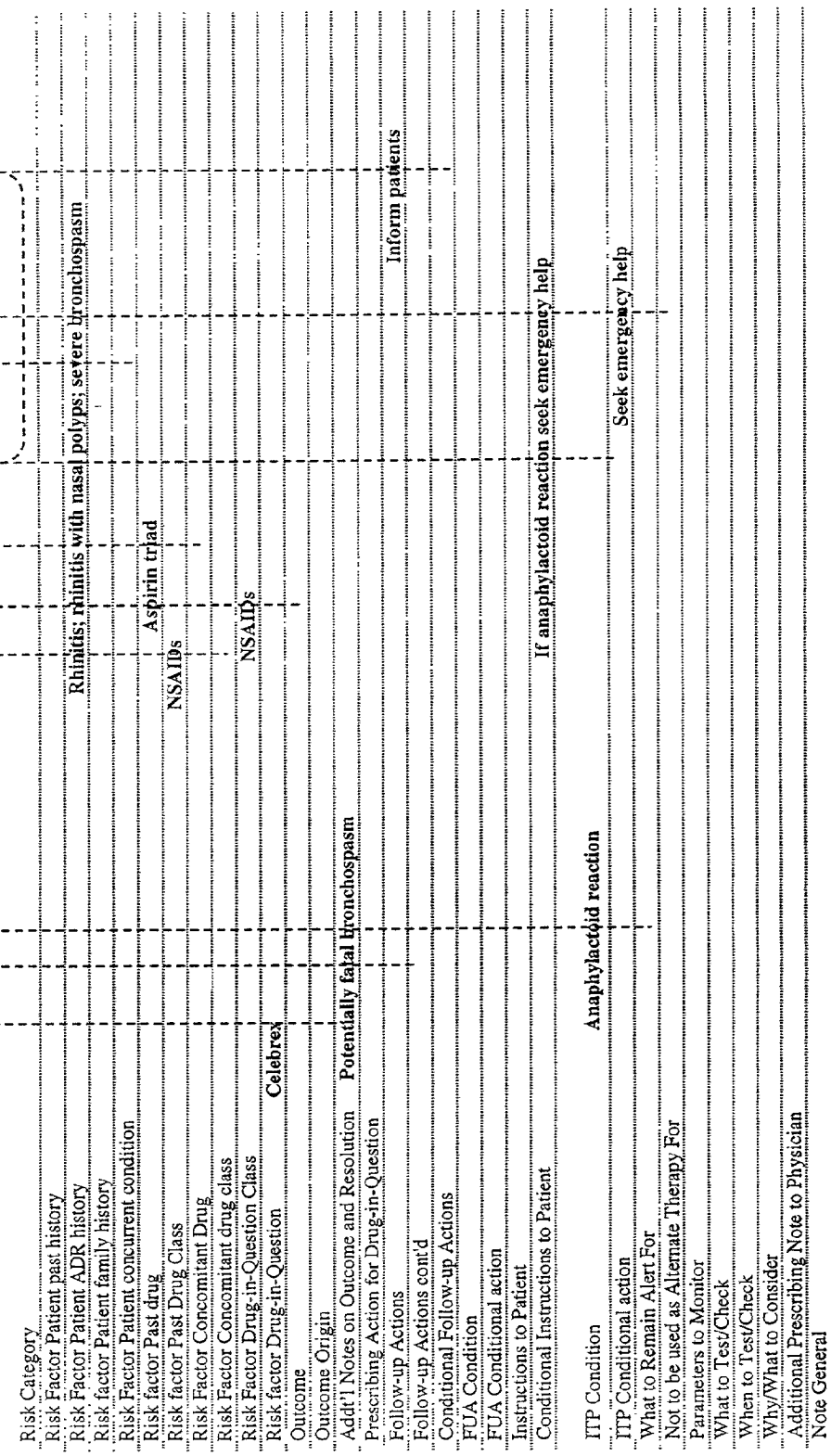

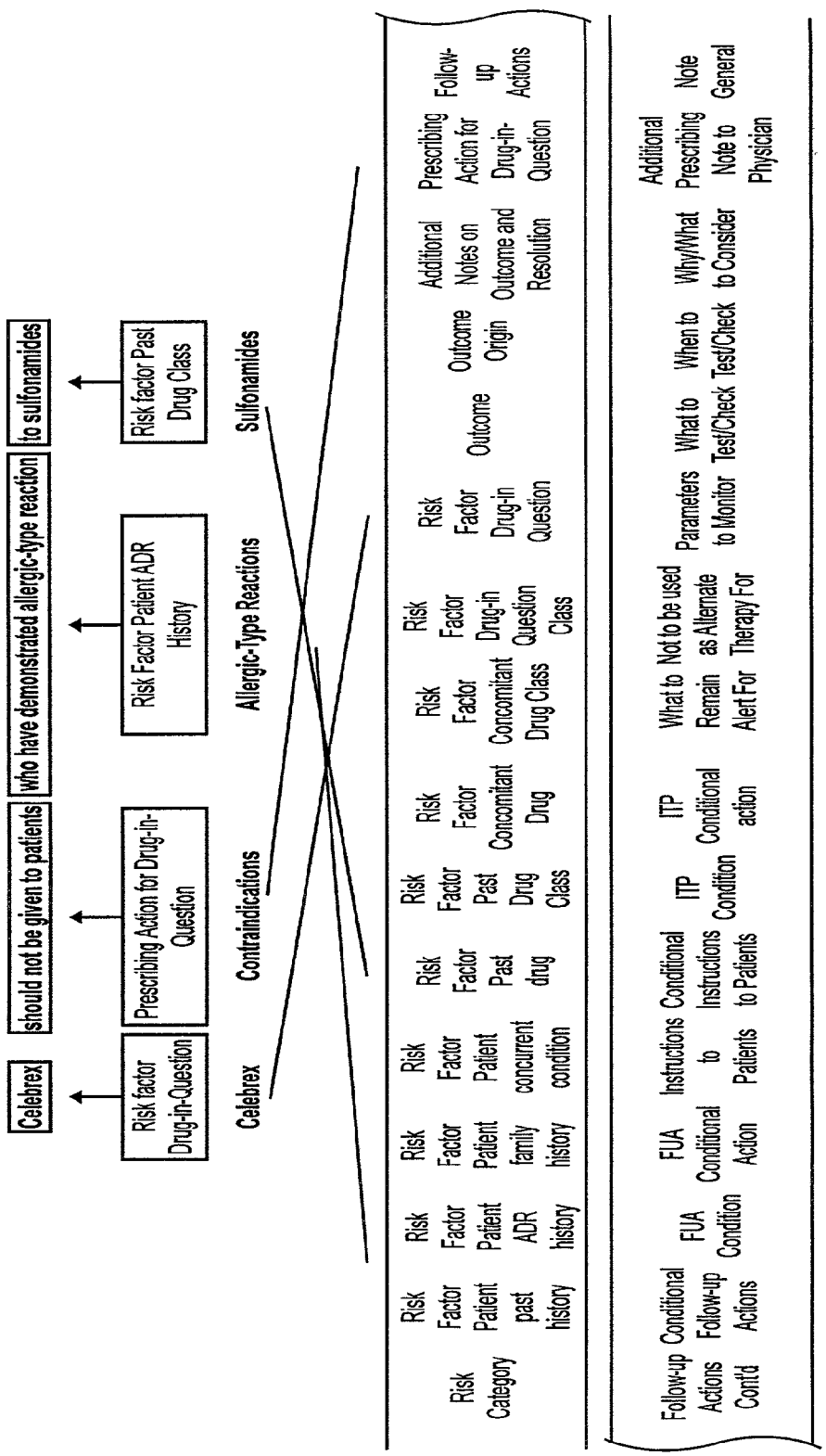
FIG. 7: Sample of reverse tracing mapping to original

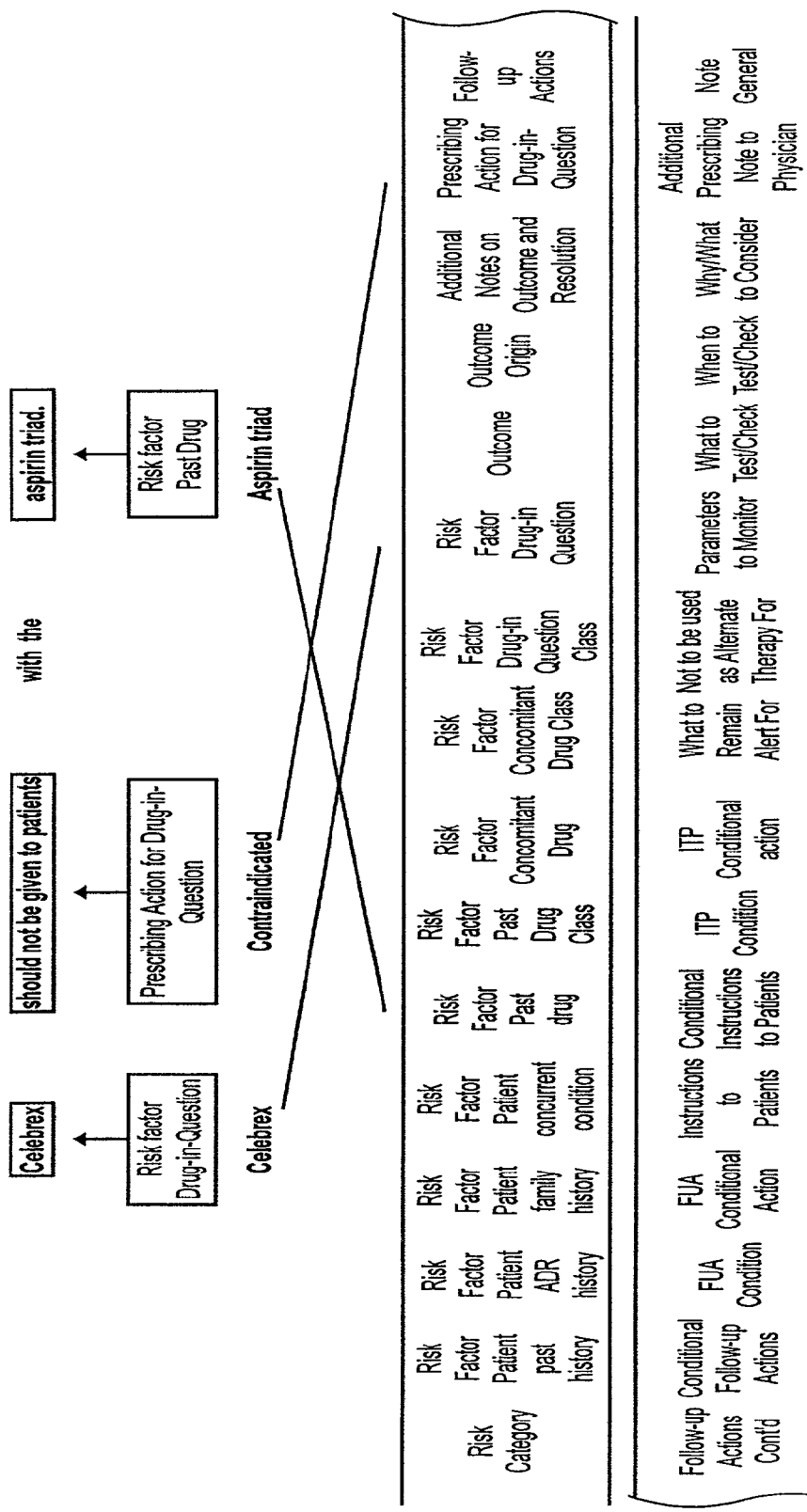
FIG. 8A: Sample of reverse tracing mapping to original label, in three parts

PROCESSING DRUG DATA

CROSS REFERENCE TO RELATED APPLICATIONS

This application is a continuation-in-part and claims priority to U.S. utility patent application Ser. No. 09/681,587, U.S. Pat. No. 6,778,994 entitled Pharmacovigilance Database, filed May 2, 2001; and incorporates the disclosure of that application by reference in its entirety.

BACKGROUND OF INVENTION

1. Field of the Invention

The present invention relates generally to systems and methods for processing drug information. More specifically, it relates to extracting data from drug information sources in a manner to support use of the data with artificial intelligence tools.

2. Background

Over 9,500 prescription drug products have been approved by the U.S. Food and Drug Administration (FDA). Label data for each drug is prepared by the drug manufacturer and approved by the FDA. Navigating through label data to locate information relevant to a prescribing decision, e.g., appropriate selection, dosing, cross-drug effects, contraindications, and warnings, is a daunting task for physicians, pharmacists, pharmaceutical benefit managers, hospital formularies, insurance companies, and others.

Compilations of label data are available. The Physicians' Desk Reference® (PDR) compiles full-length entries of the exact copy of most drug's FDA-approved label in hard copy. Computer-searchable versions of this data are available from the publisher of the PDR®; while computer-searchable versions of similar data are available from vendors such as Multum Information Services, Inc. Denver, Colo. and ePocrates, Inc., San Carlos, Calif.

Other drug information sources are available, such as articles from medical journals and formularies used by insurance carriers and health maintenance organizations (HMOs).

Each of these drug information sources may contain explicit and implicit information. For example, the drug label for RUBEX® doxorubicin hydrochloride for injection includes the following adverse event content in text form:

ADVERSE REACTIONS . . . Cutaneous: Reversible complete alopecia occurs in most cases. . . . Gastrointestinal: Acute nausea and vomiting occurs frequently and may be severe.

The adverse event content above contains implicit information regarding an adverse event, e.g., alopecia, and its frequency of occurrence when the drug is used, i.e., most.

As a further example, the drug label for REMICADE™ infliximab includes the following adverse event data content in table form:

| ADVERSE REACTIONS IN CROHN'S DISEASE TRAILS | | |
|---|---|---|
| | Placebo (n = 56) | Infliximab (n = 199) |
| ... | | |
| Pts with ≧ 1 AE WHOART preferred term | 35 (62.5%) | 168 (84.4%) |
| Headache | 12 (21.4%) | 45 (22.6%) |
| ... | | |

As another example, consider the drug label for PROZAC fluoxetine hydrochloride. Label adverse reaction information is given both explicitly in tables that contain percentages, and implicitly by use of the words frequent, infrequent, and rare.

In addition to adverse event data content, drug information sources, such as labels, typically contain instances of drug rule content. Instances of drug rule content include prose containing one or more drug rules. As an example consider the drug label for ENBREL® etanercept. Its label contains the following drug rule content

CONTRAINDICATIONS

ENBREL should not be administered to patients with sepsis or with known hypersensitivity to ENBREL or any of its compounds.

Typical existing approaches to managing drug information present the information in a simple manner, e.g., in a "warehouse" fashion, and do not focus on indirect or implicit information (especially adverse event data and drug rules). More specifically, existing approaches do not focus on capturing drug information in a manner amenable to use with artificial intelligence tools. Existing approaches typically focus on categorizing verbatim text without regard to the underlying logical content.

In addition, differing terminology employed by data authors also makes conventional queries cumbersome and the results less reliable than desired. This problem is acute in the area of medical information related to substances such as drugs. Drugs and other therapeutic substances may be known by a variety of names. In addition to the chemical name, many drugs have several clinical names recognized by health care professionals in the field. It is not uncommon for a drug to have several different trade names depending on the manufacturer. This matter is further complicated by one or more functional names that may be associated with a drug or other substance. For example, an antidepressant may be identified as Prozac®, a fluoxetine, a serotonin reuptake inhibitor, or a serotonin receptor specific modulator. However, antidepressants include many other drugs, such as lithium and other catecholaminergic drugs, and there are serotonin reuptake inhibitors in addition to Prozac®. Even "standardized" terminology can differ between compilations. For example, references that can serve as sources of standard terminology include Medical Dictionary for Regulatory Activities (MedDRA™), World Health Organization Adverse Reaction Terminology (WHO-ART), or Coding Symbols for a Thesaurus of Adverse Reaction Terms (COSTART) developed and maintained by the FDA's Center for Drug Evaluation and Research.

Typically, compilers of drug label data make minimal, if any, effort to improve the quality of the data. Data corruption can include extraneous non-alpha characters, noise words, misspellings, and dislocations (e.g., data that is valid for one category, erroneously entered into another, inappropriate field).

In addition, existing methods of compiling and organizing such data do not focus on the rules regarding drug safety contained within drug information sources. Existing approaches typically focus on categorizing verbatim text without regard to the underlying logical content.

Existing methods, alone or in combination, do not address improving the quality of the underlying verbatim drug information source data. Nor do existing methods address mapping this underlying data to accepted pharmaceutical community terms and hierarchies through which to direct queries. The problem of differing terminology among the disparate labels also remains un-addressed; as does the problem of data corruption in the form of misspelling and extraneous characters.

Typical existing methods of processing drug information are not focused on extracting rules or adverse event data from drug information sources. Nor do those methods address structuring these rules in a format amenable to use by inference engines, reasoning engines, or other similar sophisticated data processing techniques.

In view of the above-described deficiencies associated with data concerning drugs and other substances associated with medical databases, there is a need to solve these problems and enhance the amenability to efficient use of such data. These enhancements and benefits are described in detail herein below with respect to several alternative embodiments of the present invention.

SUMMARY OF INVENTION

The present invention in its disclosed embodiments alleviates the drawbacks described above with respect to existing drug information databases and incorporates several additionally beneficial features.

In some embodiments, the invention includes computer-assisted methods of processing a drug information source into syntax-parsed drug rules. The method includes creating a drug rule syntax; detecting drug rule content from the drug information source; and parsing drug rule elements from drug rule content into the drug rule syntax. In those embodiments, the associations between those drug rule elements that form a drug rule are retained.

In other embodiments, the invention includes computer-assisted methods of processing a drug information source into adverse event characterizations. In those embodiments, the method includes: detecting adverse event content from the drug information source and parsing adverse event characterizations.

In further embodiments, the invention includes computer-assisted methods for processing a drug information source to characterize the drug by the set comprising: syntax-parsed drug rule elements, adverse event data, mapped terms, and metadata. In those embodiments, the method includes: creating a drug rule syntax; extracting metadata from the drug information source; extracting verbatim adverse event data from the drug information source; identifying drug rule content from the drug information source; mapping terms from verbatim data to a reference source; and parsing drug rule elements from at least one identified instance of drug rule content into the drug rule syntax, retaining associations between those drug rule elements that form a drug rule.

It is an object of the present invention to rationalize drug information source data into a structure amenable to efficient query. In addition, a feature of preferred embodiments of the invention is that processing data in a fashion of the invention permits more than just effective database query. It permits operations to be performed on the data, e.g., calculations, comparisons, rule triggering. For example, forward and backward chaining inference engines require a rules base, Fuzzy logic requires a probabilistic or lexical way to assess closeness. Neural networks require taxonomies that allow for propagation of information though the network. Analogical reasoning, or case-based reasoning, requires a format to describe stories or situations whose relevance can be calculated using known techniques.

It is an object of the present invention to develop a drug database amenable to query using canonical terms accepted in the pharmaceutical industry. Linking terms to standard vocabulary for data such as drug name and reaction enables meaningful statistical comparisons to be made.

The beneficial effects described above apply generally to the exemplary systems and methods for developing a drug database. The specific structures through which these benefits are delivered will be described in detail hereinbelow.

BRIEF DESCRIPTION OF DRAWINGS

The invention will now be described in detail, by way of example without limitation thereto and with reference to the attached figures.

FIG. 3 is an example of parsing detected instances of rule content as drug rule elements into a syntax.

FIG. 4 is an illustrative data flow diagram of preferred embodiments of the present invention.

FIG. 5 is an illustrative data flow diagram of preferred embodiments of the present invention.

FIG. 6 is an example of parsing detected instances of rule content as drug rule elements into a syntax.

FIG. 7 is an illustrative data flow diagram of preferred embodiments of the present invention.

FIG. 8A-8C is an illustrative data flow diagram of preferred embodiments of the present invention.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a basis for the claims and as a representative basis for teaching one skilled in the art to variously employ the present invention.

Figure 1:
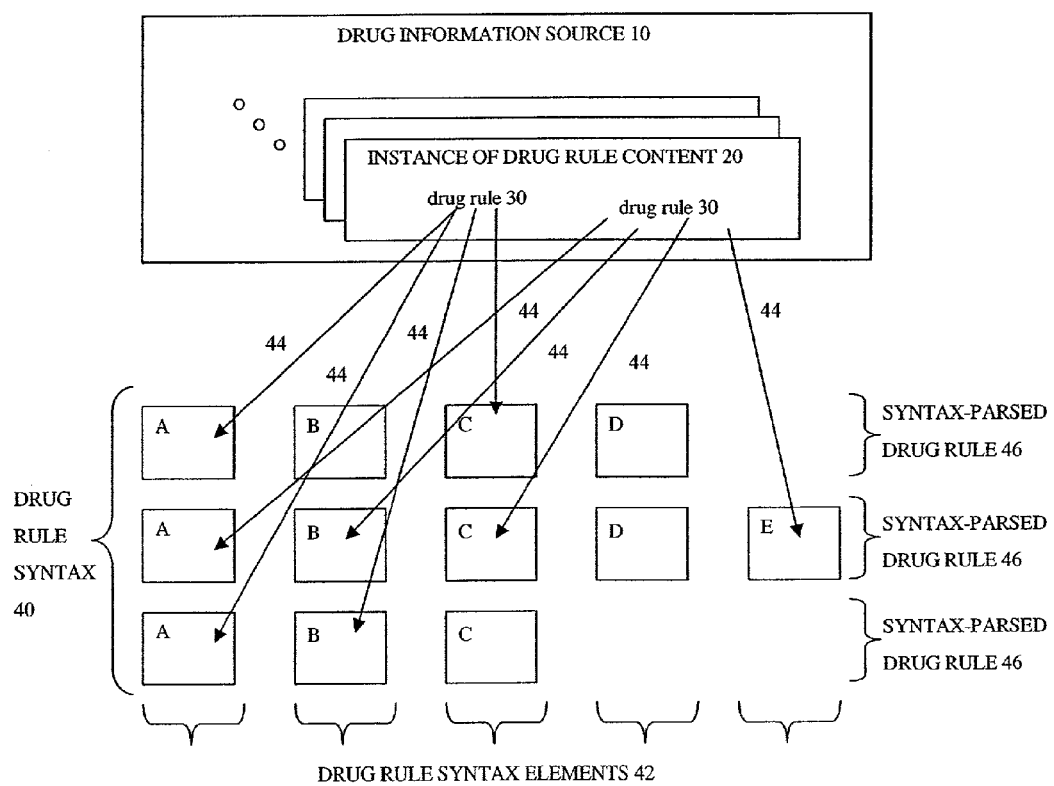
FIG. 1 is a conceptual relationship diagram of preferred embodiments of the present invention for processing drug rules.

In a preferred embodiment, the present invention includes a computer-assisted method of processing a drug information source. As illustrated in FIG. 1, a drug information source 10 typically includes at least one instance of drug rule content 20. For example, the drug label (a drug information source 10 for ENBREL® brand etanercept includes the following drug rule content 20.

"CONTRAINDICATIONS

ENBREL should not be administered to patients with sepsis or with know hypersensitivity to ENBREL or any of its components."

Each instance of drug rule content 20 includes one or more specific drug rules 30. The immediately prior example includes the following drug rule.

"ENBREL should not be administered to patients with sepsis"

In preferred embodiments, a drug rule syntax 40 is established. The drug rule syntax 40 comprises types of subsets of logical propositions, i.e., drug rule syntax elements 42, along with the allowable relationships between the types. The drug rule syntax 40 provides structure amenable to use by artificial intelligence engines. In the present example, the type <drug in question> can be instantiated as ENBREL®, the type <concurrent condition> can be an instantiated as sepsis, and the type <prescribing action for drug in question> can be instantiated as should not be administered. For this example, a syntax rule may be stated as a proposition constructed as:

For every patient p, if p (has <concurrent condition> and <drug in question> is considered), then <drug in question> <prescribing action>.

Figure 2:
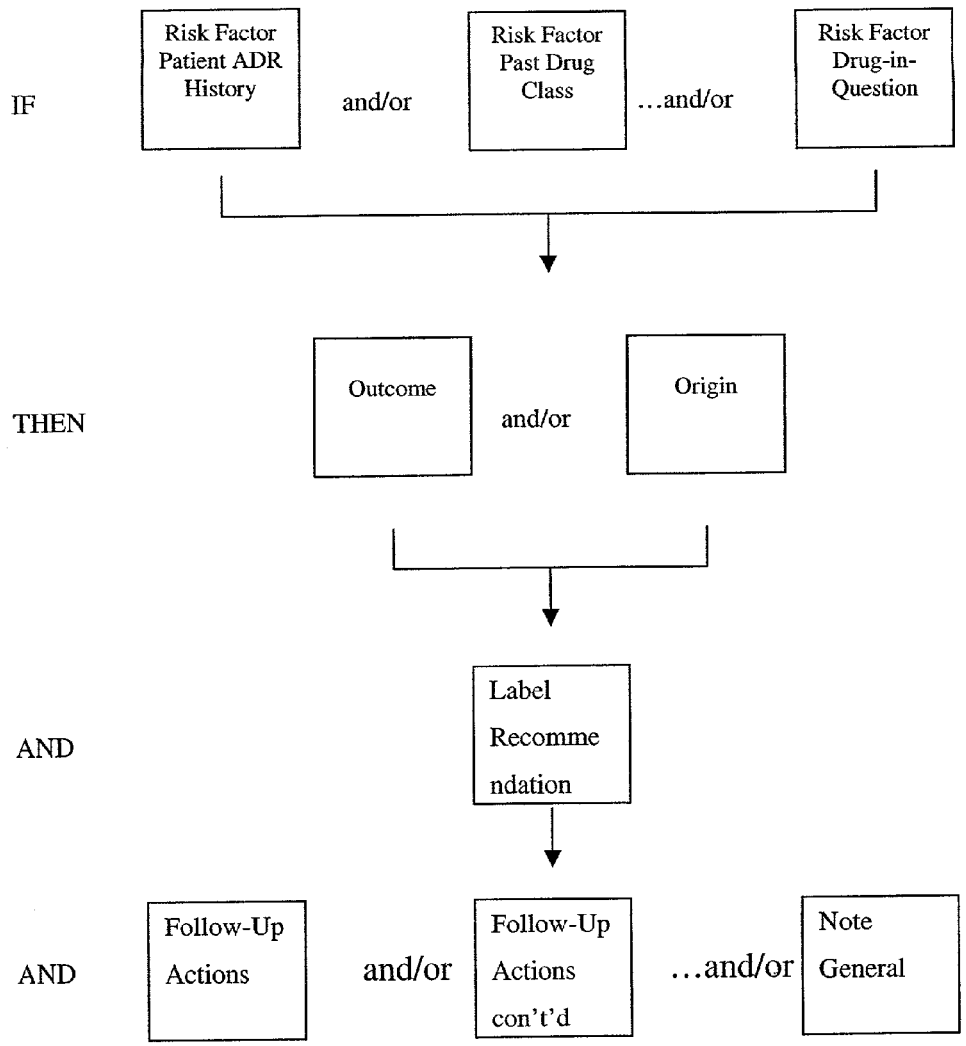
FIG. 2 is an example of a rule structure.

FIG. 2 illustrates another example of a rule structure.

Returning to FIG. 1, given a drug information source 10 (e.g., a drug label, a medical journal article, a formulary) and a syntax 40, preferred methods of the present invention include detecting at least one instance of drug rule content 20 from a drug information source 10. This step can be accomplished manually or interactively in a computer-assisted manner. Natural language processing (NLP) is suited to providing computer assistance at this step. NLP processes keying on phrases such as "should not be administered" or keying on all sentences under a heading CONTRAINDICATION can suggest sections of text as candidate drug rule content.

In preferred embodiments, instances of drug rule elements 44 are parsed from detected instances of drug rule content 20 into the drug rule syntax 40. The associations between those instances of drug rule elements 44 that form an instance of a drug rule 46 are retained. Using the immediately prior example for ENBREL®, the set of drug rule elements {<drug in question>=ENBREL, <concurrent condition>=sepsis, <prescribing action>=should not be administered} is saved and associated with a proposition of the type constructed above. Further examples of parsing from drug rule content 20 to a drug rule syntax are illustrated in FIGS. 3-8. FIG. 3 illustrates a complete parsing, into syntax elements, of the drug rule content:

"CONTRAINDICATIONS

ENBREL should not be administered to patients with sepsis or with know hypersensitivity to ENBREL or any of its components."

FIG. 4 illustrates a complete parsing of the drug rule content:

WARNINGS . . .

PATIENTS WHO DEVELOP A NEW INFECTION WHILE UNDERGOING TREATMENT WITH ENBREL SHOULD BE MONITORED CLOSELY. ADMINISTRATION OF ENBREL SHOULD EB DISCONTINUED IF A PATIENT DEVELOPS SERIOUS INFECTION OR SEPSIS. . . .

FIG. 5 illustrates a method of preferred embodiments of the present invention for processing rule content from a drug information source. In this example, either a user or a natural language processor detects words that are related to the standardized terms associated with the syntax elements. These terms or phrases are then mapped parsed into appropriate elements of the syntax. If an extracted term matches a standardized term, then it is used. If not, then it is linked to a standardized term. The mapping between the verbatim text and the structured rule is retained as a pedigree for treacability.

Figure 8B:
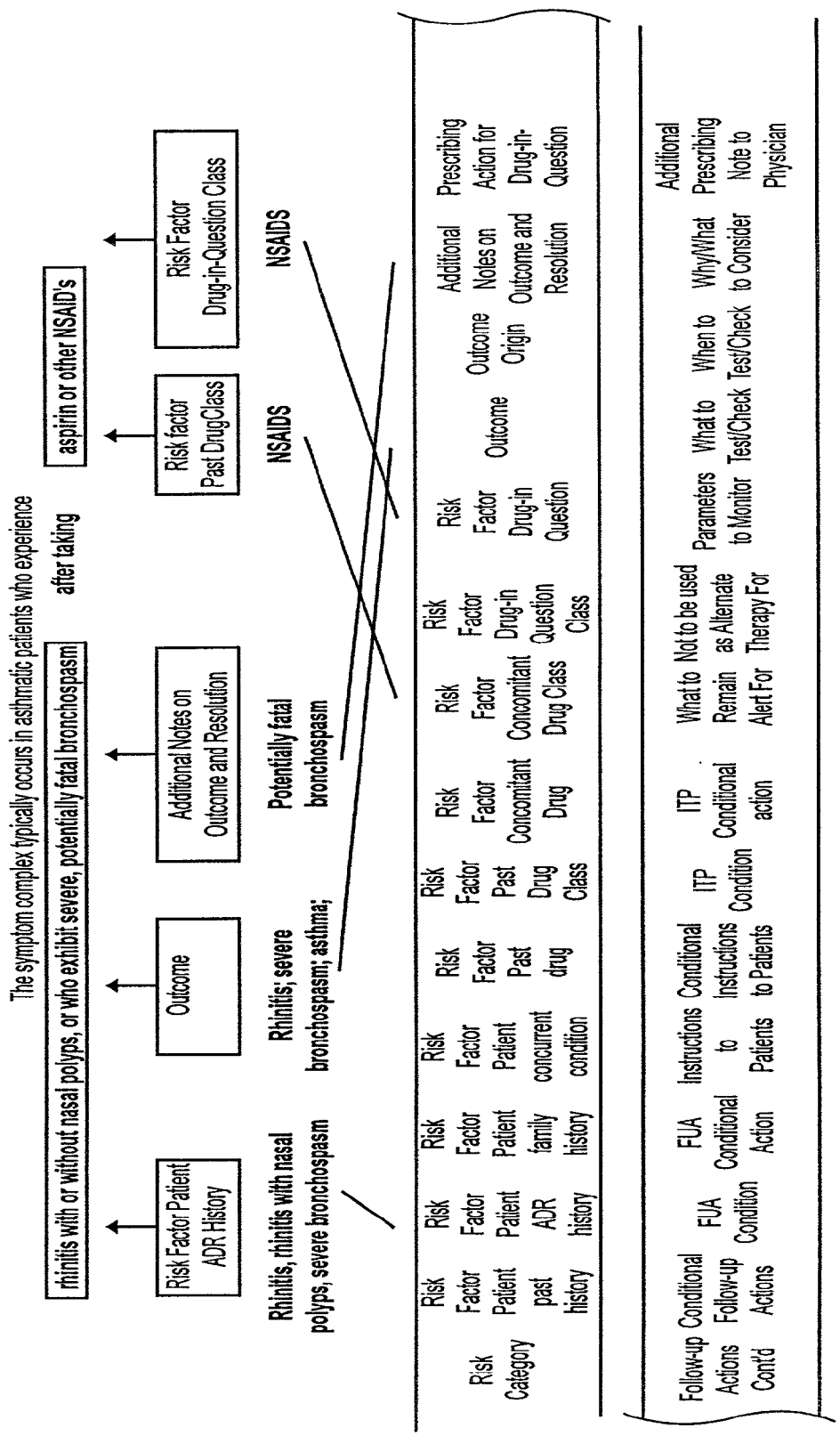
Figure 8C:
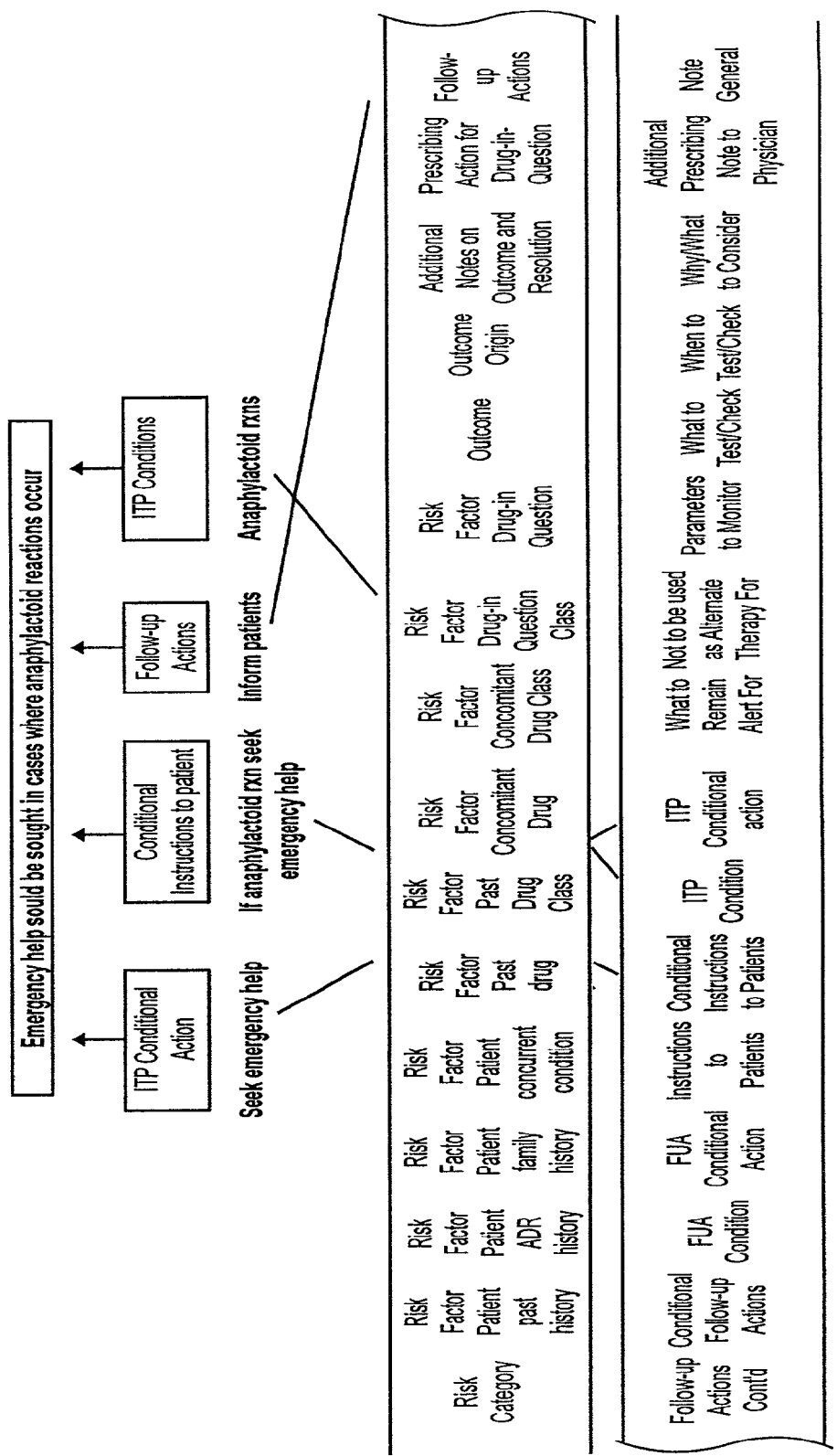

FIGS. 6, 7, and 8 show additional examples of parsing. FIG. 8 uses a horizontal mapping in a simple spreadsheet to show parsing without the use of natural language processing.

Figure 9:
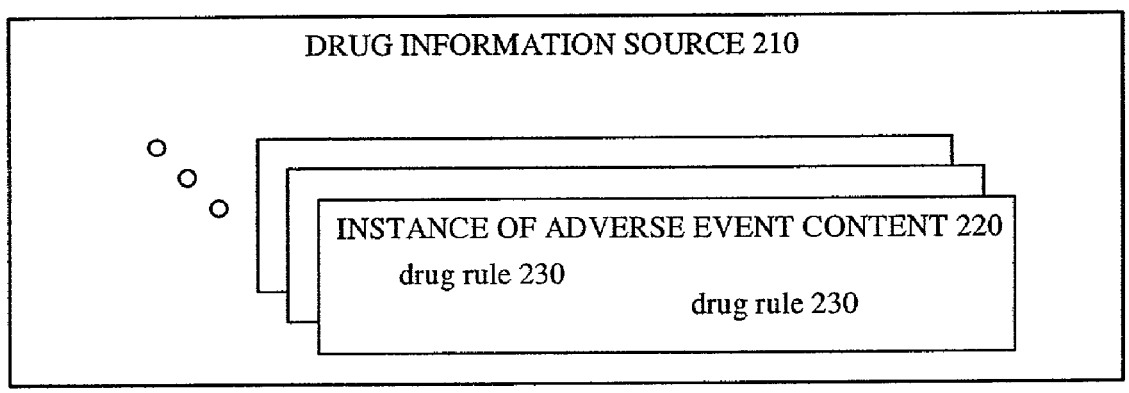
FIG. 9 is a conceptual relationship diagram of preferred embodiments of the present invention for processing adverse event data.

In some embodiments, the invention includes a computer-assisted method of processing a drug information source for extracting adverse event characterizations in a format amenable to use with artificial intelligence engines. Referring to FIG. 9, the drug information source 210 comprising at least one instance of adverse event content 220. For example, the drug label (a drug information source 210) for ENBREL® brand etanercept includes the following instances of adverse event content 220 in table form.

| Percent of RA Patients Reporting Adverse Events . . . | | |
|---|---|---|
| | Percent of patients | |
| Event | Placebo (n = 152) | ENBREL (n = 349) |
| Injection Site reaction | 10 | 37 |
| Infection | 32 | 35 |

Each instance of adverse event content 220 includes least one adverse event characterization 230. In the above example, the set {ENBREL, injection site reaction, 37%} is an adverse event characterization. This is an example of an adverse event characterization of the form {<drug in question>, <adverse event>, <frequency>}.

The drug label information for ENBREL® also includes the following adverse event content, in text form:

ADVERSE REACTIONS . . .

Other Adverse Reactions . . .

Other infrequent serious adverse events observed included: heart failure, myocardial infarction, . . .

In this case, the adverse event characterization is quantitatively implicit and not quantitatively explicit, i.e., heart attack is characterized as infrequent as opposed to 1%. However, other information sources, such as accepted practice within the medical field or policy within a particular organization, may interpret infrequent as corresponding to a range of less than 2%. An exemplary characterization of heart failure with respect to ENBREL® in such a case would be {ENBREL, heart failure, infrequent} or {ENBREL, heart failure, <2%}. Specific representations would be tailored to particular applications, e.g., <2% could be represented by a range of 0%-1.99%, i.e., a lower and upper range limit.

Preferred embodiments of the present invention include detecting instances of adverse event content from a drug information source. As with detection of drug rule content, this step can be accomplished manually or interactively in a computer-assisted manner. Natural language processing (NLP) is suited to providing computer assistance at this step. NLP processes keying on phrases such as "% " or keying on all sentences under a heading ADVERSE REACTIONS can suggest sections of text as candidate drug rule content. In some embodiments, the method described above is executed more than once as a validation, preferably involving interaction with different human users.

Figure 10:
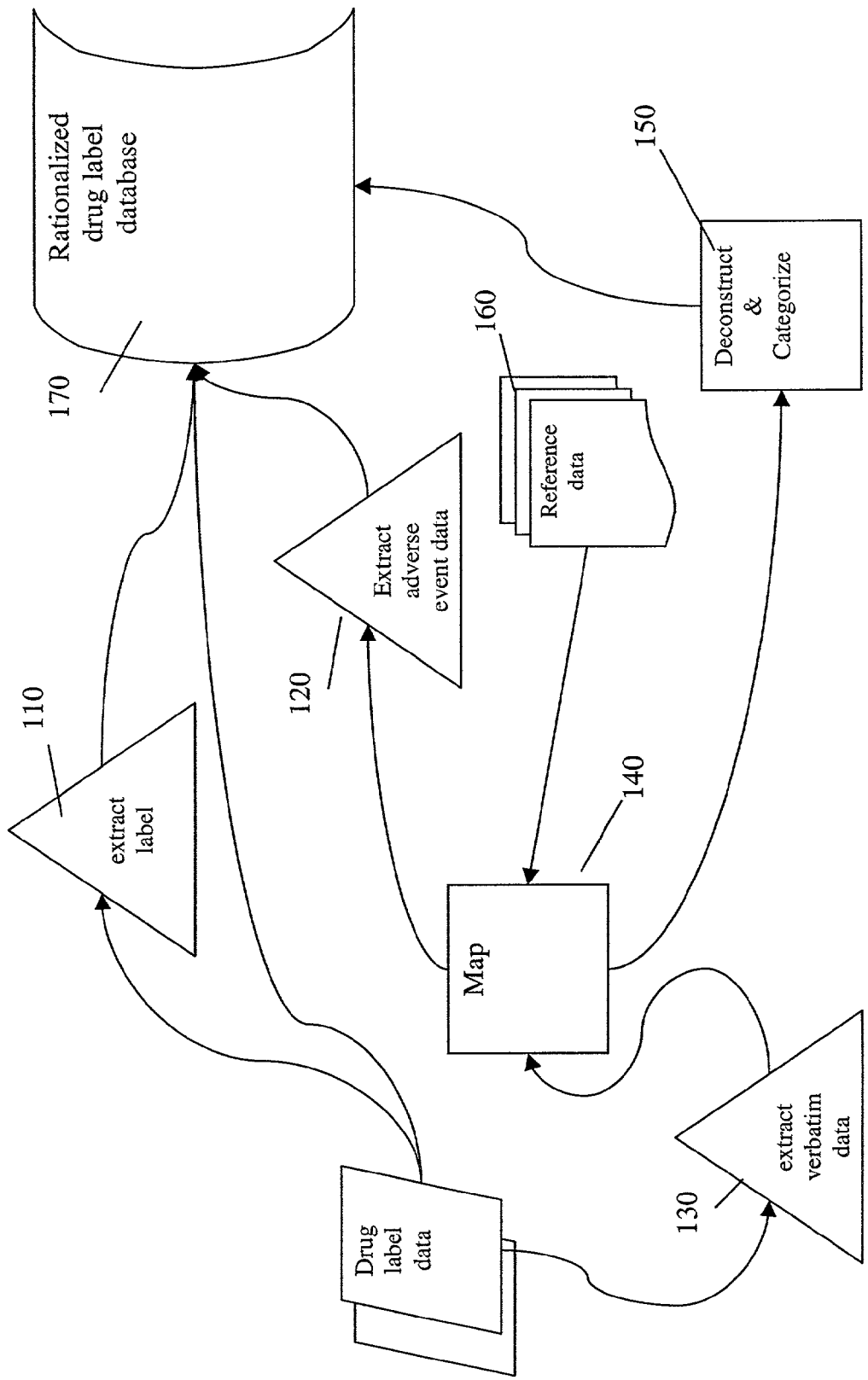
FIG. 10 is an illustrative data flow diagram of preferred embodiments of the present invention.

Referring to FIG. 10, drug information sources 300 are typically associated with data about the information source, i.e., drug information source metadata, such as revision date or version. For example, the entry for Merrem® in the 2000 edition of PDR® indicates that the label version is "Rev E 3/99." Embodiments of the present invention extract 310 such drug information source metadata as one element to characterize the drug in a rationalized database 370.

Drug information sources may also typically contain descriptions of:
  circumstances that provide the basis for initiation of a treatment using the drug, i.e., indications;
  symptoms or circumstance that renders the use of a drug inadvisable, i.e., contraindications;
  factors a practitioner should consider when prescribing a drug, i.e., precautions and warnings.

Given that verbatim terms referring to the same condition, compound, symptom, etc. may vary across labels (and even within a label), preferred embodiments of the present invention provide mapping 340 from verbatim drug information source 300 terms to a set of standard terms that will serve as a basis for query. The combination of verbatim terms data mapped to standard token terms serves as a thesaurus. In one embodiment, MedDRA™ serves as the set of standard terms 360. In other embodiments, a user may select the dictionary of reference terms 360.

Transparency in the process of moving from source data verbatim terms to a cleaned safety database with verbatim terms mapped to tokens is important to both database developers/operators and to end users. Preferred embodiments of the present invention capture the way source data terms have been cleaned and mapped as the "pedigree" of each term. The "pedigree" of a term is the link between the mapped term and the decisions made during data cleanup. End users typically wish to verify the pedigree of the data they use. In those embodiments, retained data includes one or more of the following as appropriate: verbatim term, token mapped to, source of the verbatim term, number of occurrences of the verbatim term, which type of cleanup (if any) was performed, and a cross-reference to where the token is defined.

Adverse event data, typically collected during clinical trials can be found in some drug information sources, e.g., drug labels, in both tabular and text form. Embodiments of the invention process 320 this data as described above, from the drug information sources 300 containing such data. These embodiments identify adverse event data in a manner amenable to query or use as input for an artificial intelligence engine. Drug rule data is also processed 350 in the embodiments illustrated in FIG. 3; preferably in the manner described earlier for processing drug rule data.

In preferred embodiments illustrated in FIG. 3, the full-text of the drug information source 300 (including graphs, tables, charts, pictograms) is associated 370 with the source 300 in the database. The set of adverse event data, drug rules, metadata, and full text serve to characterize the drug. The set of characterizations serves as the database to which various analytical engines (e.g., neural nets, case-based reasoning tools, and predicate calculus engines) can be applied.

Preferred embodiments of the present invention include those implemented on a single computer or across a network of computers, e.g., a local area network of the Internet. Preferred embodiments include implementations on computer-readable media storing a computer program product performing one or more of the steps described herein. Such a computer program product contains modules implementing the steps as functions inter-related as described herein. Preferred embodiments of the invention include the unique data structures described herein, encoded on a computer-readable medium and computer signals transmissible over a computer/communications network.

A method and system for rationalizing drug label data has been described herein. These and other variations, which will be appreciated by those skilled in the art, are within the intended scope of this invention as claimed below. As previously stated, detailed embodiments of the present invention are disclosed herein; however, it is to be understood that the disclosed embodiments are merely exemplary of the invention that may be embodied in various forms.

The invention claimed is:

1. A computer-assisted method of processing a drug information source, the method comprising:

creating a drug rule syntax comprising (a) drug rule syntax elements, each corresponding to a subset of a logical proposition, and (b) allowable logical relationships between said drug rule syntax elements;

detecting at least one instance of drug rule content from a drug information source; and parsing drug rule elements from at least one identified instance of drug rule content into the drug rule syntax, retaining associations described in said drug rule content between drug rule elements that form a drug rule, whereby a subset of the drug information source is processed into syntax-parsed drug rules.

2. The method of claim 1 wherein drug source information comprises at least one of: drug label information; and drug literature information.

3. A computer-assisted method of processing a drug information source, the drug information source comprising at least one instance of adverse event content, each instance of adverse event content comprising at least one adverse event characterization, the method comprising:

creating a drug rule syntax comprising (a) drug rule syntax elements, each corresponding to a subset of a logical proposition, and (b) allowable logical relationships between said drug rule syntax elements;

detecting at least one instance of adverse event content from a drug information source; and parsing at least one adverse event characterization from at least one detected instance of adverse event content, whereby a subset of the drug information source is processed into at least one parsed adverse event characterization, and wherein the at least one adverse event characterization comprises quantitatively explicit information.

4. The method of claim 3 further comprising: validating at least one parsed adverse event characterization.

5. The method of claim 3, wherein: adverse event content comprises text content, and each adverse event characterization comprises the set of reaction name and frequency of occurrence characterization.

6. The method of claim 3, wherein: adverse event content comprises text content, and at least one adverse event characterization comprises the set of reaction name, lower limit frequency of occurrence, and higher limit frequency of occurrence.

7. The method of claim 3, wherein: adverse event content comprises table content, and at least one adverse event characterization comprises the set of reaction name, and nominal frequency of occurrence.

8. The method of claim 3, wherein: adverse event content comprises table content, and at least one adverse event characterization comprises the set of reaction name, lower limit frequency of occurrence, and higher limit frequency of occurrence.

9. The method of claim 3, wherein at least one instance of adverse event content comprises an implicit adverse event characterization, and the method further comprises deriving an adverse event characterization from the implicit adverse characterization.

10. The method of claim 9, wherein: the derived adverse event characterization comprises the set of reaction name, and nominal frequency of occurrence.

11. The method of claim 9, wherein: the derived adverse event characterization comprises the set of reaction name, lower limit frequency of occurrence, and higher limit frequency of occurrence.

12. A method for processing a drug information source, the method comprising creating a drug rule syntax comprising (a) drug rule syntax elements, each corresponding to a subset of a logical proposition, and (b) allowable logical relationships between said drug rule syntax elements;

extracting metadata from the drug information source;

extracting verbatim adverse event data from the drug information source;

identifying at least one instance of drug rule content from the drug information source; mapping terms from verbatim data to a reference source;

parsing drug rule elements from at least one identified instance of drug rule content into the drug rule syntax, retaining associations described in said drug rule content between those drug rule elements that form a drug rule;

wherein the drug described by the drug information source is characterized by the set comprising: the syntax-parsed drug rule elements, the mapped terms, and the metadata.

13. The method of claim 12, wherein: the reference source comprises MedDRA.

14. The method of claim 12, wherein: the reference source is selectable by a user.

15. The method of claim 12, wherein: the mapping between a reference source term and the corresponding verbatim identifies the pedigree of each reference source term-verbatim pair.

16. The method of claim 12, further comprising: associate remaining drug information source data with the drug wherein the drug described by the drug information source is characterized by the set comprising: the syntax-parsed drug rule elements, the mapped terms, the metadata, and the remaining drug information source data.

* * * * *